(12) United States Patent
Chen et al.

(10) Patent No.: US 11,555,008 B2
(45) Date of Patent: Jan. 17, 2023

(54) METHOD FOR PREPARING L-CARNITINE USING MICRO-REACTION SYSTEM

(71) Applicant: Fudan University, Shanghai (CN)

(72) Inventors: Fener Chen, Shanghai (CN); Dang Cheng, Shanghai (CN); Minjie Liu, Shanghai (CN); Meifen Jiang, Shanghai (CN); Zedu Huang, Shanghai (CN); Zexu Wang, Shanghai (CN); Jiaqi Wang, Shanghai (CN)

(73) Assignee: Fudan University, Shanghai (CN)

( * ) Notice: Subject to any disclaimer, the term of this patent is extended or adjusted under 35 U.S.C. 154(b) by 195 days.

(21) Appl. No.: 17/123,098

(22) Filed: Dec. 15, 2020

(65) Prior Publication Data
US 2021/0380524 A1 Dec. 9, 2021

(30) Foreign Application Priority Data
Jun. 5, 2020 (CN) .......................... 202010503112.4

(51) Int. Cl.
*B01J 19/00* (2006.01)
*C07C 227/04* (2006.01)
*C07C 229/22* (2006.01)

(52) U.S. Cl.
CPC ......... *C07C 227/04* (2013.01); *B01J 19/0093* (2013.01); *B01J 2219/0086* (2013.01); *B01J 2219/00869* (2013.01); *B01J 2219/00889* (2013.01); *C07C 229/22* (2013.01)

(58) Field of Classification Search
CPC .... B01J 19/00; B01J 19/0093; B01J 2219/00; B01J 2219/00781; B01J 2219/00788; B01J 2219/00792; B01J 2219/00851; B01J 2219/00858; B01J 2219/0086; B01J 2219/00869; B01J 2219/00889; B01J 2219/0095; B01J 2219/00952; B01J 2219/00954; B01J 2219/00961; B01J 2219/00963; B01J 2219/00984; C07C 227/00; C07C 227/04; C07C 227/06; C07C 227/08; C07C 229/00; C07C 229/02; C07C 229/04; C07C 229/22
See application file for complete search history.

(56) References Cited

U.S. PATENT DOCUMENTS

| | | |
|---|---|---|
| 4,710,468 A | 12/1987 | Sih |
| 4,895,979 A | 1/1990 | Noyori et al. |
| 2002/0165408 A1 | 11/2002 | Tinti et al. |

FOREIGN PATENT DOCUMENTS

| | | | |
|---|---|---|---|
| CN | 100348573 C | 11/2007 | |
| CN | 102952028 A | 3/2013 | |
| CN | 103012177 B | 4/2015 | |
| CN | 110003032 A | * 7/2019 | ........... C07C 213/04 |

(Continued)

OTHER PUBLICATIONS

Bing Nan Zhou, Aravamudan S. Gopalan, Frank VanMiddlesworth, Woan Ru Shieh, and Charles J. Sih Stereochemical control of yeast reductions. 1. Asymmetric synthesis of L-carnitine J. Am. Chem. Soc. 1983, 105, 18, 5925-5926.

*Primary Examiner* — Natasha E Young

(57) ABSTRACT

A method for preparing L-carnitine using a micro-reaction system. (R)-4-halo-3-hydroxybutyrate was subjected to quaternization and hydrolysis in an aqueous trimethylamine solution in the presence of an inorganic base in a micro-channel reactor to produce the L-carnitine.

20 Claims, 5 Drawing Sheets

(56) References Cited

FOREIGN PATENT DOCUMENTS

| EP | 0339764 | A1 | 11/1989 |
|---|---|---|---|
| JP | 1989211551 | A | 8/1989 |
| JP | 1990142758 | A | 5/1990 |
| WO | 0029370 | A1 | 5/2000 |
| WO | 2007139238 | A1 | 12/2007 |

* cited by examiner

METHOD FOR PREPARING L-CARNITINE USING MICRO-REACTION SYSTEM

CROSS-REFERENCE TO RELATED APPLICATIONS

This application claims the benefit of priority from Chinese Patent Application No. 202010503112.4, filed on Jun. 5, 2020. The content of the aforementioned application, including any intervening amendments thereto, is incorporated herein by reference in its entirety.

TECHNICAL FIELD

The present application relates to preparation of L-carnitine, and more particularly to a method for preparing L-carnitine using a micro-reaction system.

BACKGROUND

As a key transmitter in the fat metabolism, levocarnitine, also known as L-carnitine or vitamin $B_T$, mainly plays a role in promoting the oxidation and decomposition of fatty acids in mitochondria to provide energy for cells. L-carnitine is widely used in the treatment of carnitine deficiency and various ischemic heart diseases, liver disease, kidney disease and dyskinesia characterized by muscle weakness, etc. It can also be used as an additive in food and feed. With regard to the preparation of L-carnitine, International Patent No. 2007/139238, U.S. Pat. No. 4,895,979, EP Patent No. 0339764, and JP Patent No. 1989211551 all disclosed that (R)-4-halo-3-hydroxybutyrate underwent quaternization in an aqueous solution containing 27%-30% by weight of trimethylamine, and then the resultant product was hydrolyzed in the presence of hydrochloric acid to obtain L-carnitine. Though this method had shortened reaction time (3-5 hours), the yield of L-carnitine was relatively low (only 46% at most). In the method proposed by International Patent No. 00/29370 and US Patent No. 2002/0165408, (R)-4-halo-3-hydroxybutyrate underwent the above-mentioned two steps in an aqueous solution containing 45% by weight of trimethylamine to prepare L-carnitine, in which the yield of L-carnitine was greatly increased to 70-75%, but the reaction time was as long as 24-60 hours. In U.S. Pat. No. 4,710,468, a solution of (R)-4-halo-3-hydroxybutyrate in methanol or ethanol and an aqueous solution containing 25% by weight of trimethylamine were subjected to the abovementioned two-step reaction to prepare the L-carnitine. However, the yield of L-carnitine decreased significantly when the process was scaled up to a hectogram scale, and is thus not suitable for industrial production. Chinese Patent No. 100348573C and Chinese Patent Publication No. 102952028A both disclosed a method for preparing L-carnitine by reacting (R)-4-chloro-3-hydroxybutyrate with a trimethylamine aqueous solution in the presence of an inorganic base. This method had a relatively high yield, but the reaction needed to be completed at low temperature for 24-48 hours, bringing low efficiency and high energy consumption.

JP Patent No. 1990142758 and Chinese Patent No. 103012177B respectively disclosed a method for preparing L-carnitine through a gas-liquid reaction of a (R)-4-chloro-3-hydroxybutyrate organic solution and trimethylamine gas in the presence of an organic base. The total yield of L-carnitine can reach 69-76%, but the reaction conditions were harsh and the operation is complicated. Zhou et al. from University of Wisconsin-Madison (*J. Am. Chem. Soc.* 1983, 105: 5925-5926) has reported that octyl (R)-4-chloro-3-hydroxybutyrate reacted with a solution of trimethylamine in ethanol to prepare L-carnitine, and the total yield was not satisfactory (only 45%). In summary, the above methods all are carried out in a traditional batch stirred reactor, and have the drawbacks of complicated operation, long quaternization time, excessive side reactions and low yield.

SUMMARY

In view of the shortcomings in the prior art, the disclosure provides a method for preparing L-carnitine using a micro-reaction system. Compared to the prior art, the method provided herein has shortened reaction time, significantly improved yield and simple operation, and thus is suitable for industrial production. It should be particularly noted that there is no report on the continuous preparation of L-carnitine through quaternization with trimethylamine and hydrolysis using a micro-channel reactor.

The technical solutions of the application are described as follows.

The disclosure provides a method for preparing L-carnitine using a micro-reaction system, the micro-reaction system comprising a first micro-mixer and a micro-channel reactor in communication; the method comprising.

(1) pumping a (R)-4-halo-3-hydroxybutyrate and an aqueous trimethylamine solution containing an inorganic base into the first micro-mixer simultaneously followed by mixing to obtain a mixture; and (2) allowing the mixture flowing out of the first micro-mixer to enter the micro-channel reactor; and subjecting the mixture to continuous quaternization and hydrolysis to obtain the L-carnitine;

wherein the (R)-4-halo-3-hydroxybutyrate is shown in formula (I):

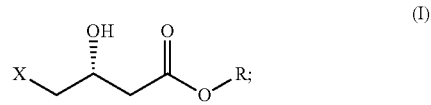

wherein X is F, Cl, Br or I, and R is a $C_1$-$C_4$ alkyl.

The preparation of L-carnitine (II) provided herein is shown in the following reaction scheme:

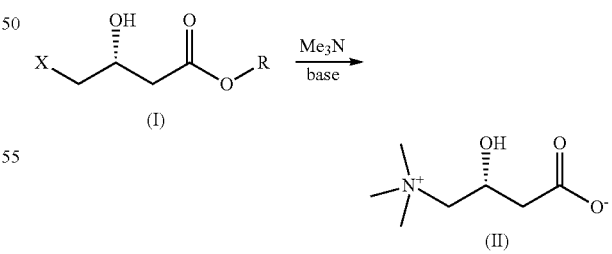

In some embodiments, in step (1), the (R)-4-halo-3-hydroxybutyrate is ethyl (R)-4-chloro-3-hydroxybutyrate; and the inorganic base is an alkali metal carbonate, an alkali metal hydroxide or a combination thereof.

In an embodiment, in step (1), the inorganic base is selected from the group consisting of lithium carbonate, sodium carbonate, potassium carbonate, lithium bicarbonate, sodium bicarbonate, potassium bicarbonate, lithium hydroxide, sodium hydroxide, potassium hydroxide and a combination thereof.

In some embodiments, in step (1), a molar ratio of (R)-4-halo-3-hydroxybutyrate to trimethylamine is (0.1-5):1; and a molar ratio of (R)-4-halo-3-hydroxybutyrate to the inorganic base is (0.2-1.2):1.

In an embodiment, in step (1), the molar ratio of (R)-4-halo-3-hydroxybutyrate to trimethylamine is (0.2-3):1; and the molar ratio of (R)-4-halo-3-hydroxybutyrate to the inorganic base is (0.3-0.95):1.

In some embodiments, in step (1), the aqueous trimethylamine solution comprises 3%-45%, preferably 4%-30%, by weight of trimethylamine.

In some embodiments, in step (2), a temperature in the micro-channel reactor is −40° C.-100° C., preferably −20° C.-60° C., and a residence time of the reaction mixture in the micro-channel reactor is 0.2-30 min, preferably 0.5-20 min.

In some embodiments, in step (2), a backpressure in the micro-channel reactor is 0.1-3 MPa, preferably 0.2-2.5 MPa.

In some embodiments, the method further comprises:
adjusting the reaction mixture flowing out of the micro-channel reactor to pH 6-8 with a pH regulator.

In some embodiments, the pH regulator is an acidic pH regulator, preferably an aqueous hydrochloric acid solution, and more preferably a 7%-10% aqueous hydrochloric acid solution.

In some embodiments, the micro-reaction system further comprises a second micro-mixer, an outlet of the micro-channel reactor is communicated with an inlet of the second micro-mixer; and the pH adjustment is carried out in the second micro-mixer.

In some embodiments, a total pressure drop of the first micro-mixer, the micro-channel reactor and the second micro-mixer is 0-0.7 MPa, preferably 0.001-0.5 MPa.

In some embodiments, the second micro-mixer is a T-shaped or Y-shaped mixer; the outlet of the micro-channel reactor is communicated with a first inlet of the second micro-mixer, and a second inlet of the second micro-mixer is configured to allow the pH regulator to be pumped in.

In some embodiments, the first micro-mixer comprises a first liquid inlet channel and a second liquid inlet channel parallel to each other; one end of the first liquid inlet channel is provided with a first liquid inlet, and the other end of the first liquid inlet channel is closed; one end of the second liquid inlet channel is provided with a second liquid inlet, and the other end of the second liquid inlet channel is provided with a liquid outlet; the first liquid inlet and the second liquid inlet are arranged at the same end; a wall is shared by the first liquid inlet channel and the second liquid inlet channel, and a plurality of micro pores are provided at the wall to communicate the first liquid inlet channel with the second liquid inlet channel; in step (1), the (R)-4-halo-3-hydroxybutyrate is pumped into the first liquid inlet channel, and the aqueous trimethylamine solution containing the inorganic base is pumped into the second liquid inlet channel; the (R)-4-halo-3-hydroxybutyrate in the first liquid inlet channel flows through the micro pores into the second liquid inlet channel, and then mixes with the inorganic base-containing aqueous trimethylamine solution in the second liquid inlet channel.

In some embodiments, the micro pores are circular.

In some embodiments, a hydraulic diameter of each of the plurality of micro pores is 0.1-300 μm, preferably 0.2-250 μm, and a distance between adjacent two micro pores is 0.1 μm-1.5 mm, preferably 0.2 μm-1.4 mm.

In some embodiments, opening areas of the plurality of micro pores are 1%-70%, preferably 2%-65%, of an area of the wall.

In some embodiments, a cross section of the first liquid inlet channel is circular or rectangular, and a cross section of the second liquid inlet channel is circular or rectangular.

In some embodiments, a hydraulic diameter of the first liquid inlet channel is 0.01-20 mm, preferably 0.02-15 mm, and a hydraulic diameter of the second liquid inlet channel is 0.01-20 mm, preferably 0.02-15 mm.

In some embodiments, a ratio of the hydraulic diameter of each of the plurality of micro pores to the hydraulic diameter of the second liquid inlet channel is 0.0001-0.1:1, preferably 0.0375-0.1:1.

In some embodiments, a length of the first liquid inlet channel is 2-30 mm, preferably 3-28 mm, and a length of the second liquid inlet channel is 4-100 mm, preferably 5-80 mm.

In some embodiments, the micro-channel reactor is a tubular micro-channel reactor or a plate micro-channel reactor.

In some embodiments, an inner diameter of the tubular micro-channel reactor is 100 μm-10 mm, preferably 120 μm-5.35 mm.

In some embodiments, a hydraulic diameter of a reaction fluid channel of the plate micro-channel reactor is 100 μm-10 mm, preferably 120 μm-5.35 mm.

The above-mentioned technical solutions bring the following beneficial effects.

The method provided herein adopts a micro-reaction system to prepare L-carnitine, in which the reaction can be quantitatively completed within a few minutes with a yield more than 95%. Compared to the prior art, the method provided herein has greatly shortened reaction time (only several minutes) and significantly improved yield of the L-carnitine, and the side reaction is suppressed to the greatest extent. In addition, the multiphase mixing, mass transfer and reaction of the reaction materials are completed in the micro-mixer and micro-channel reactor, which has the advantages of simple and continuous operation, low cost, high automation degree and high efficiency. The conventional stirring device is not necessary, which simplifies the production equipment and reduces the energy consumption.

Figure 1:
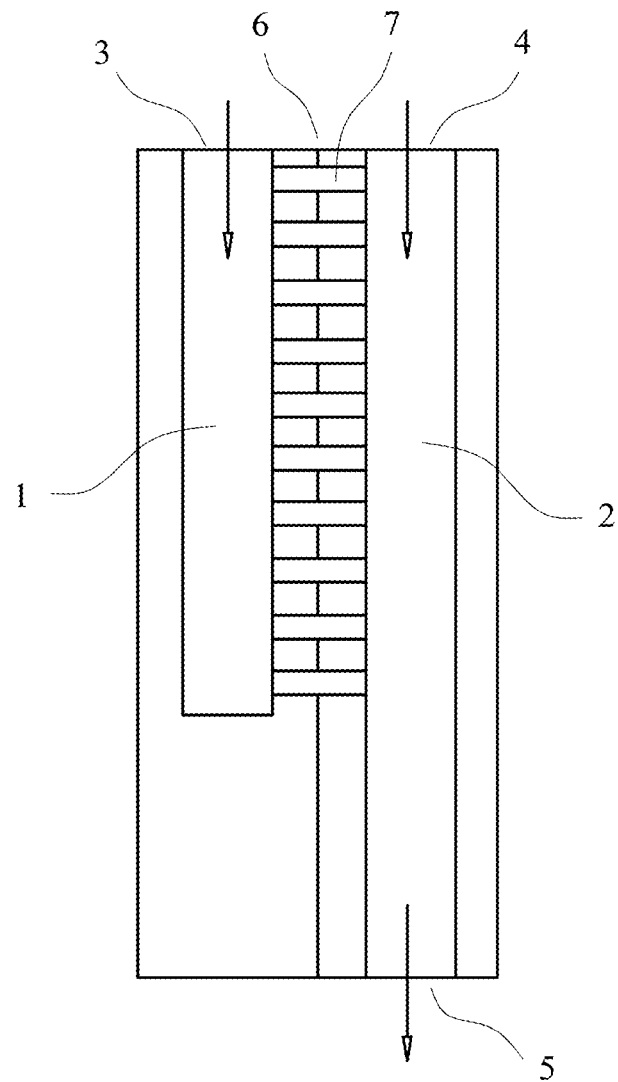
FIG. 1 is a schematic diagram of a first micro-mixer in accordance with an embodiment of the disclosure.

In the drawings; 1, first liquid inlet channel; 2, second liquid inlet channel; 3, first liquid inlet; 4, second liquid inlet; 5, liquid outlet of the second liquid inlet channel; 6, wall; 7, micro pore; 8, first micro-mixer; 9, tubular micro-channel reactor; 10, second micro-mixer; 11, thermostatic oil bath; 12, plate micro-channel reactor; 13, first temperature-control medium layer; 14, reaction layer; 15, second temperature-control medium layer; 16, third micro-mixer; 17, storage tank; and 18, pump.

DETAILED DESCRIPTION OF EMBODIMENTS

To explain the object, technical solution and advantages of the invention better, the invention will be further described below in detail with reference to the embodiments.

As shown in FIG. 1, a first micro-mixer includes a first liquid inlet channel 1 and a second liquid inlet channel 2 parallel to each other. One end of the first liquid inlet channel 1 is provided with a first liquid inlet 3, and the other end is closed. One end of the second liquid inlet channel 2 is provided with a second liquid inlet 4, and the other end is provided with a liquid outlet 5. The first liquid inlet 3 and the second liquid inlet 4 are arranged at the same end. A wall 6 is shared by the first liquid inlet channel 1 and the second liquid inlet channel 2, and a micro pore 7 is provided at the wall 6 to communicate the first liquid inlet channel 1 with the second liquid inlet channel 2. The liquid in the first liquid inlet channel 1 is able to flow into the second liquid inlet channel 2 through the micro pore, and then is mixed with the liquid in the second liquid inlet channel 2.

In some embodiments, the micro pore 7 is a circular.

In some embodiments, there are a plurality of micro pores 7 provided at the wall 6 to communicate the first liquid inlet channel 1 and the second liquid inlet channel 2. In some embodiments, a hydraulic diameter of the micro pore 7 is 0.1-300 μm, preferably 0.2-250 μm, and more preferably 15-40 μm, and a distance between the adjacent two micro pores 7 is 0.1 μm-1.5 mm, preferably 0.2 μm-1.4 mm.

In some embodiments, opening areas of the micro pores 7 are 1-70%, preferably 2-65%, of an area of the wall 6. As used herein, the percentage refers to a ratio of the total opening area of the micro pores 7 on one side of the wall 6 to the area of the side of the wall 6.

In some embodiments, a cross section of the first liquid inlet channel 1 is circular or rectangular, and a cross section of the second liquid inlet channel 2 is circular or rectangular.

In some embodiments, a hydraulic diameter of the first liquid inlet channel 1 is 0.01-20 mm, preferably 0.02-15 mm, and a hydraulic diameter of the second liquid inlet channel 2 is 0.01-20 mm, preferably 0.02-15 mm.

In some embodiments, a ratio of the hydraulic diameter of the micro pore 7 to the hydraulic diameter of the second liquid inlet channel 2 is 0.0001-0.1:1, preferably 0.0375-0.1:1.

In some embodiments, a length of the first liquid inlet channel 1 is 2-30 mm, preferably 3-28 mm, and a length of the second liquid inlet channel 2 is 4-100 mm, preferably 5-80 mm.

The first micro-mixer 8 is configured to enable the fluid in the first liquid inlet channel 1 to be dispersed into the liquid in the second liquid inlet channel 2 in the form of micro droplets to form a micro dispersion system. Compared with a conventional micro-mixer, the first micro-mixer of the disclosure can greatly enhance the liquid-liquid mass transfer process by shortening the mass transfer distance and improving the mass transfer area based on the micro droplets with high dispersibility and high specific surface area. Therefore, the first micro-mixer can effectively enhance the liquid-liquid reaction process.

When the first micro-mixer shown in FIG. 1 is used, (R)-4-halo-3-hydroxybutyrate enters the first liquid inlet channel 1 through the first liquid inlet 3, and the trimethylamine aqueous solution enters the second liquid inlet channel 2 from the second liquid inlet 4. After filling the first liquid inlet channel 1, (R)-4-halo-3-hydroxybutyrate is driven to enter the second liquid inlet channel 2 through the micro pore 7 under the action of pressure, and then forms a (R)-4-halo-3-hydroxybutyrate micro droplet dispersion system in the second liquid inlet channel 2 under the shearing action of the inorganic base-containing aqueous trimethylamine solution. The resultant micro droplet dispersion system has an extremely large specific surface area and mass transfer coefficient, so that the two fluids can be efficiently mixed and reacted, thus shortening the reaction time and improving the yield of L-carnitine.

Example 1

Figure 2:
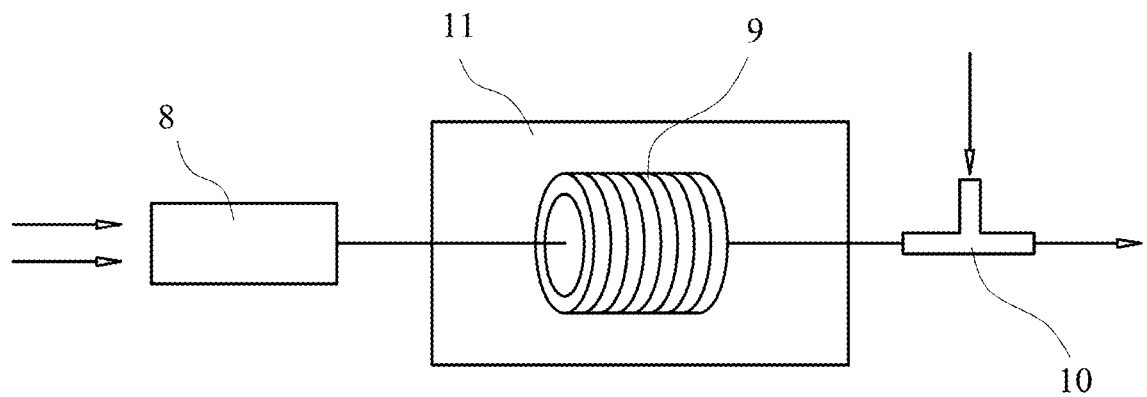
FIG. 2 is a schematic diagram of a micro-reaction system in accordance with an embodiment of the disclosure.

Provided herein was a method for preparing L-carnitine using a micro-reaction system as shown in FIG. 2, where the micro-reaction system included a first micro-mixer 8, a tubular micro-channel reactor 9 and a second micro-mixer 10 that were communicated in sequence. The first micro-mixer 8 was shown in FIG. 1. The tubular micro-channel reactor 9 was made of 316 L stainless steel tubular micro-channel reactor, and had an outer diameter of 1.6 mm, an inner diameter of 1.0 mm, and a total volume of 7.85 mL. The micro-reaction system also included a thermostatic oil bath 11, which was configured to adjust and control the temperature in the tubular micro-channel reactor 9. The second micro-mixer 10 was a T-type mixer.

The method was specifically described as follows.

(1) An aqueous sodium hydroxide solution with a mass percentage concentration of 4.77% and an aqueous hydrochloric acid solution with a mass percentage concentration of 10% were prepared. Trimethylamine gas was introduced into the aqueous sodium hydroxide aqueous solution to prepare an aqueous trimethylamine solution with a mass percentage concentration of 12%.

(2) The sodium hydroxide-containing trimethylamine solution prepared in step (1) and ethyl (R)-4-chloro-3-hydroxybutyrate were simultaneously pumped into the first micro-mixer 8 and mixed, where volume flow rates of the two reactants were adjusted separately to ensure that a molar ratio of ethyl (R)-4-chloro-3-hydroxybutyrate to trimethylamine was 0.25:1.

(3) The reaction mixture flowing out of the first micro-mixer 8 immediately entered the tubular micro-channel reactor 9 for continuous quaternization and hydrolysis, where a temperature in the tubular micro-channel reactor 9 was 10° C., and a back pressure was 0.3 MPa. The reaction mixture underwent quaternization and hydrolysis while flowing in the tubular micro-channel reactor 9, and flowed out from the outlet of the tubular micro-channel reactor 9 after residing for 7 min.

(4) The reaction mixture flowing out of the tubular micro-channel reactor 9 entered the second micro-mixer 10. At the same time, the aqueous hydrochloric acid solution with a mass percentage concentration of 10% was pumped into the second micro-mixer 10, and adjusted in the flow rate to adjust the pH of the reaction mixture to 6 to obtain L-carnitine.

Contents of the substrate and the target compound in the resultant reaction mixture were analyzed by LC (Agilent) based on peak area. The results showed that the substrate (R)-4-halo-3-hydroxybutyrate experienced a complete conversion, and the target compound L-carnitine had a yield of 95.4%. Moreover, a total pressure drop of the first micro-mixer 8, the tubular micro-channel reactor 9 and the second micro-mixer 10 was 0.06 MPa.

Example 2

Provided herein was a method for preparing L-carnitine using a micro-reaction system as shown in FIG. 2, where the micro-reaction system included a first micro-mixer 8, a tubular micro-channel reactor 9 and a second micro-mixer 10 communicated in sequence. The first micro-mixer 8 was shown in FIG. 1. The tubular micro-channel reactor 9 was made of polytetrafluoroethylene (PTFE), and had an outer diameter of 1.6 mm, an inner diameter of 0.9 mm and a total volume of 9.54 mL. The micro-reaction system also included a thermostatic oil bath 11, which was configured to adjust and control the temperature in the tubular micro-channel reactor 9. The second micro-mixer 10 was a T-type mixer.

The method was specifically described as follows.

(1) An aqueous sodium hydroxide solution with a mass percentage concentration of 6.34% and an aqueous hydrochloric acid solution with a mass percentage concentration of 8% were prepared. Trimethylamine gas was introduced into the aqueous sodium hydroxide solution to prepare an aqueous trimethylamine solution with a mass percentage concentration of 15%.

(2) The sodium hydroxide-containing trimethylamine solution prepared in step (1) and ethyl (R)-4-chloro-3-hydroxybutyrate were pumped into the first micro-mixer 8 at the same time and mixed, where volume flow rates of the two reactants were adjusted separately to ensure that a molar ratio of ethyl (R)-4-chloro-3-hydroxybutyrate to trimethylamine was 0.3:1.

(3) After flowing out of the first micro-mixer 8, the reaction mixture immediately entered the tubular micro-channel reactor 9 and underwent continuous quaternization and hydrolysis while flowing in the tubular micro-channel reactor 9, where a temperature in the tubular micro-channel reactor 9 was 18° C., and a back pressure was 0.4 MPa. After residing for 7.3 min, the reaction mixture was discharged from the outlet of the tubular micro-channel reactor 9.

(4) The reaction mixture flowing out of the tubular micro-channel reactor 9 entered the second micro-mixer 10. At the same time, the aqueous hydrochloric acid solution with a mass percentage concentration of 8% was pumped into the second micro-mixer 10 and adjusted in the flow rate to adjust pH of the reaction mixture to obtain L-carnitine.

Contents of the substrate and the target compound in the resultant reaction mixture were analyzed by LC (Agilent) based on peak area. The results showed that the substrate (R)-4-halo-3-hydroxybutyrate experienced a complete conversion, and the target compound L-carnitine had a yield of 96.2%. Moreover, a total pressure drop of the first micro-mixer 8, the tubular micro-channel reactor 9 and the second micro-mixer 10 was 0.08 MPa.

Example 3

Provided herein was a method for preparing L-carnitine using a micro-reaction system as shown in FIG. 2, where the micro-reaction system included a first micro-mixer 8, a tubular micro-channel reactor 9 and a second micro-mixer 10 that were communicated in sequence. The first micro-mixer 8 was shown in FIG. 1. The tubular micro-channel reactor 9 was made of 304 stainless steel, and had an outer diameter of 3.2 mm, an inner diameter of 2.2 mm, and a total volume of 38 mL. The micro-reaction system also included a thermostatic oil bath 11, which was configured to adjust and control the temperature in the tubular micro-channel reactor 9. The second micro-mixer 10 was a T-type mixer.

The method was specifically described as follows.

(1) An aqueous sodium hydroxide solution with a mass percentage concentration of 3.6% and an aqueous hydrochloric acid solution with a mass percentage concentration of 7% were prepared. Trimethylamine gas was introduced into the aqueous sodium hydroxide solution to prepare an aqueous trimethylamine solution with a mass percentage concentration of 8%.

(2) The sodium hydroxide-containing trimethylamine solution prepared in step (1) and ethyl (R)-4-chloro-3-hydroxybutyrate were simultaneously pumped into the first micro-mixer 8 and mixed, where volume flow rates of the two reactants were adjusted separately to ensure that a molar ratio of ethyl (R)-4-chloro-3-hydroxybutyrate to trimethylamine was 0.32:1.

(3) The reaction mixture flowing out of the first micro-mixer 8 immediately entered the tubular micro-channel reactor 9 for continuous quaternization and hydrolysis, where a temperature in the tubular micro-channel reactor 9 was 12° C., and a back pressure was 0.5 MPa. The reaction mixture underwent quaternization and hydrolysis while flowing in the tubular micro-channel reactor 9, and flowed out of the outlet of the tubular micro-channel reactor 9 after residing for 8 min.

(4) The reaction mixture flowing out of the tubular micro-channel reactor 9 entered the second micro-mixer 10. At the same time, the aqueous hydrochloric acid solution with a mass percentage concentration of 7% was pumped into the second micro-mixer 10, and adjusted in the flow rate to adjust the pH of the reaction mixture to 6 to obtain L-carnitine.

Contents of the substrate and the target compound in the resultant reaction mixture were analyzed by LC (Agilent) based on peak area. The results showed that the substrate (R)-4-halo-3-hydroxybutyrate experienced a complete conversion, and the target compound L-carnitine had a yield of 96.2%. Moreover, a total pressure drop of the first micro-mixer 8, the tubular micro-channel reactor 9 and the second micro-mixer 10 was 0.065 MPa.

Example 4

Figure 3:
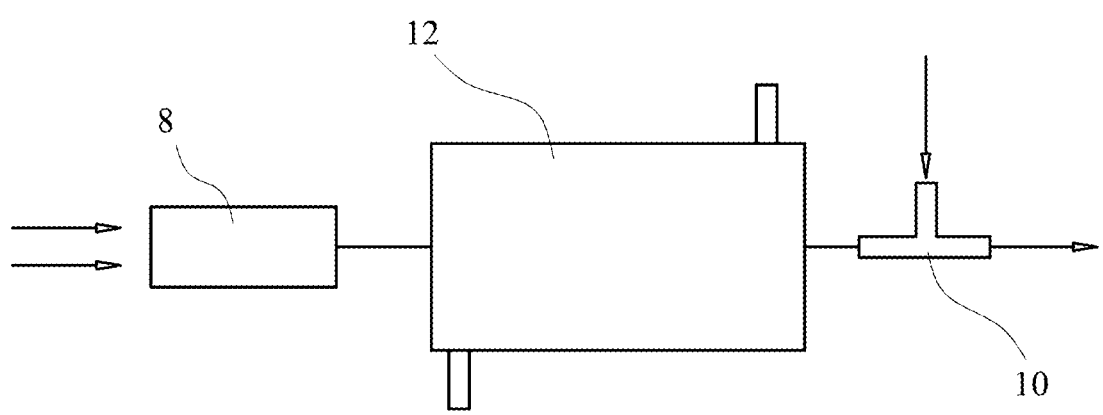
FIG. 3 is a schematic diagram of a micro-reaction system in accordance with an embodiment of the disclosure.
Figure 4:
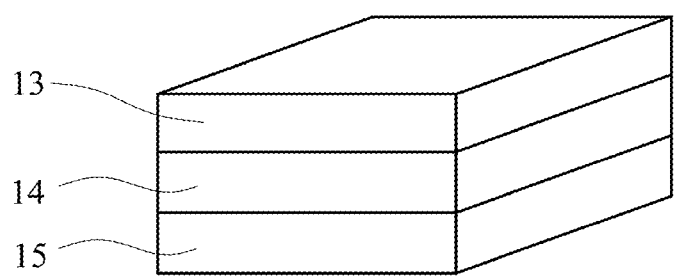
FIG. 4 is a schematic diagram of a micro-reaction system in accordance with an embodiment of the disclosure.

Provided herein was a method for preparing L-carnitine using a micro-reaction system as shown in FIG. 3, where the micro-reaction system included a first micro-mixer 8, a plate micro-channel reactor 12 and a second micro-mixer 10 communicated in sequence. The first micro-mixer 8 was shown in FIG. 1. The plate micro-channel reactor 12 was made of 316 L stainless steel, and had a cuboid structure with a length of 12 cm, a width of 10 cm and a height of 3 cm (FIG. 4). The plate micro-channel reactor 12 included a first temperature-control medium layer 13, a reaction layer 14 and a second temperature-control medium layer 15 from top to bottom. The first temperature-control medium layer 12 and the second temperature-control medium layer 15 were used to adjust and control the temperature of the reaction layer 14. The reaction layer 14 was provided with a reaction fluid channel with a cross section of 400 μm (width)×600 μm (length), a hydraulic diameter of 480 μm, and a total volume of 9.6 mL. The second micro-mixer 10 was a T-type mixer.

The method was specifically described as follows.

(1) An aqueous sodium hydroxide solution with a mass percentage concentration of 4.51% and an aqueous hydrochloric acid solution with a mass percentage concentration of 10% were prepared. Trimethylamine gas was introduced into the aqueous sodium hydroxide solution to prepare an aqueous trimethylamine solution with a mass percentage concentration of 10%.

(2) The sodium hydroxide-containing trimethylamine solution prepared in step (1) and ethyl (R)-4-chloro-3-hydroxybutyrate were pumped into the first micro-mixer 8 at the same time and mixed, where volume flow rates of the two reactants were adjusted separately to ensure that a molar ratio of ethyl (R)-4-chloro-3-hydroxybutyrate to trimethylamine was 0.25:1.

(3) After flowing out of the first micro-mixer 8, the reaction mixture immediately entered the reaction fluid channel of the plate micro-channel reactor 12 and underwent continuous quaternization and hydrolysis while flowing in the tubular micro-channel reactor 9, where a temperature in the reaction fluid channel was 15° C., and a back pressure was 0.6 MPa. After residing for 7.8 min, the reaction mixture was discharged from the outlet of the tubular micro-channel reactor 9.

(4) The reaction mixture flowing out of the reaction fluid channel entered the second micro-mixer 10. At the same time, the aqueous hydrochloric acid solution with a mass percentage concentration of 10% was pumped into the second micro-mixer 10 and adjusted in the flow rate to adjust pH of the reaction mixture to 6 to obtain L-carnitine.

Contents of the substrate and the target compound in the resultant reaction mixture were analyzed by LC (Agilent) based on peak area. The results showed that the substrate (R)-4-halo-3-hydroxybutyrate experienced a complete conversion, and the target compound L-carnitine had a yield of 96.4%. Moreover, a total pressure drop of the first micro-mixer 8, the tubular micro-channel reactor 9 and the second micro-mixer 10 was 0.084 MPa.

Example 5

Figure 5:
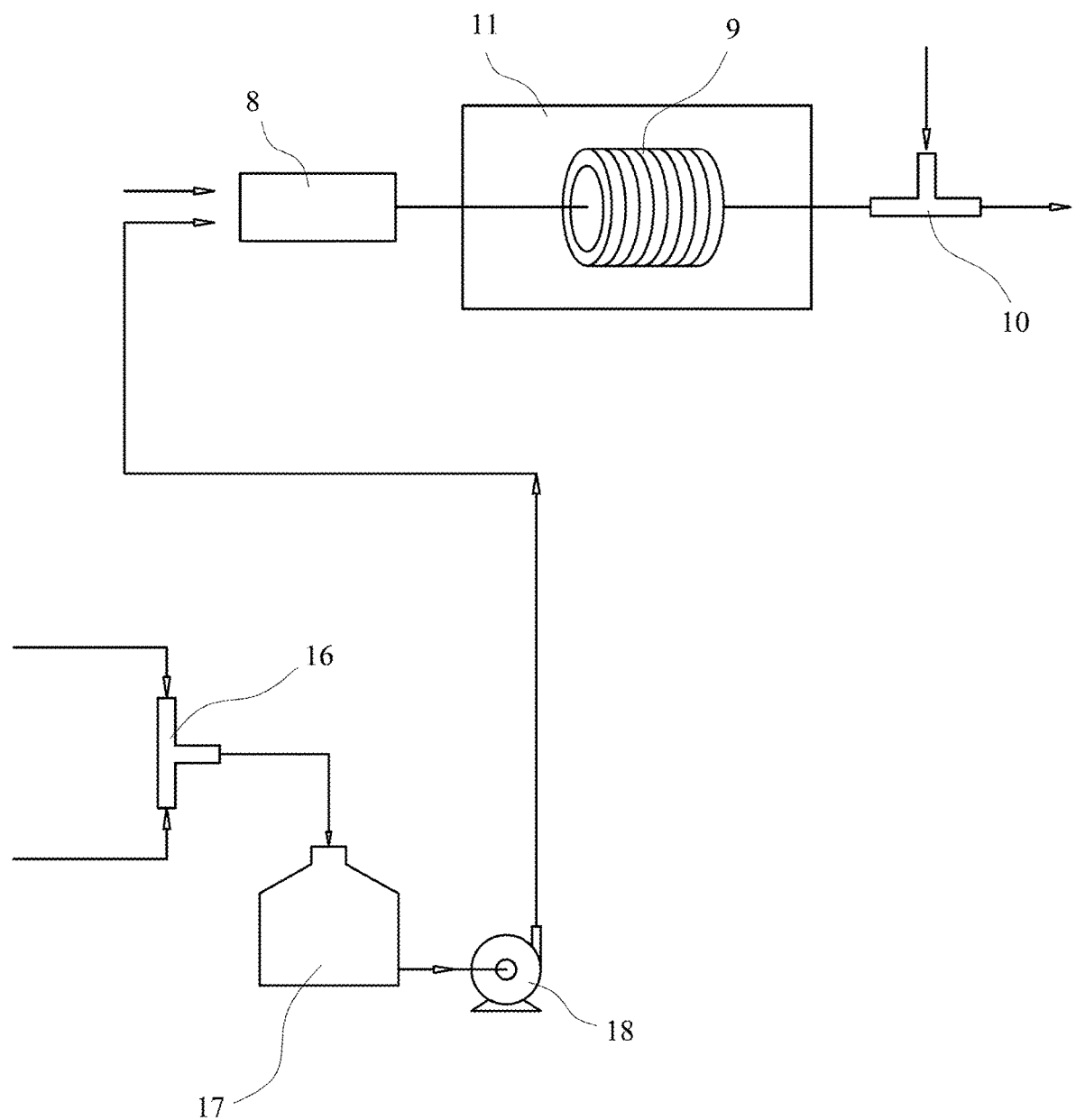
FIG. 5 is a schematic diagram of a micro-reaction system in accordance with an embodiment of the disclosure.

Provided herein was a method for preparing L-carnitine using a micro-reaction system as shown in FIG. 5, where the micro-reaction system included a third micro-mixer 16, a storage tank 17, a first micro-mixer 8, a tubular micro-channel reactor 9 and a second micro-mixer 10 communicated in sequence. The first micro-mixer 8 was shown in FIG. 1. The tubular micro-channel reactor 9 was made of 304 stainless steel, and had an outer diameter of 3.2 mm, an inner diameter of 2.2 mm and a total volume of 38 mL. The micro-reaction system also included a thermostatic oil bath 11, which was configured to adjust and control the temperature in the tubular micro-channel reactor 9. The second micro-mixer 10 and the third micro-mixer 13 were both a T-type mixer.

The method was specifically described as follows.

(1) An aqueous sodium hydroxide solution with a mass percentage concentration of 6.3% and an aqueous hydrochloric acid solution with a mass percentage concentration of 10% were prepared. Trimethylamine gas and the aqueous sodium hydroxide solution were transported to the third micro-mixer 16 and mixed, where flow rates of the trimethylamine gas flow and the aqueous sodium hydroxide solution were controlled to obtain an aqueous trimethylamine solution with a mass percentage concentration of 14.9% which was stored in a storage tank 17.

(2) The sodium hydroxide-containing trimethylamine solution prepared in step (1) and ethyl (R)-4-chloro-3-hydroxybutyrate were pumped into the first micro-mixer 8 at the same time and mixed, where volume flow rates of the two reactants were adjusted separately to ensure that a molar ratio of ethyl (R)-4-chloro-3-hydroxybutyrate to trimethylamine was 0.3:1.

(3) After flowing out of the first micro-mixer 8, the reaction mixture immediately entered the tubular micro-channel reactor 9 and underwent continuous quaternization and hydrolysis while flowing in the tubular micro-channel reactor 9, where a temperature in the tubular micro-channel reactor 9 was 11° C., and a back pressure was 0.35 MPa. After residing for 8.2 min, the reaction mixture was discharged from the outlet of the tubular micro-channel reactor 9.

(4) The reaction mixture flowing out of the tubular micro-channel reactor 9 entered the second micro-mixer 10. At the same time, the aqueous hydrochloric acid solution with a mass percentage concentration of 10% was pumped into the second micro-mixer 10 and adjusted in the flow rate to adjust pH of the reaction mixture to 6 to obtain L-carnitine.

Contents of the substrate and the target compound in the resultant reaction mixture were analyzed by LC (Agilent) based on peak area. The results showed that the substrate (R)-4-halo-3-hydroxybutyrate experienced a complete conversion, and the target compound L-carnitine had a yield of 95.6%. Moreover, a total pressure drop of the first micro-mixer 8, the tubular micro-channel reactor 9 and the second micro-mixer 10 was 0.078 MPa.

Example 6

Figure 6:
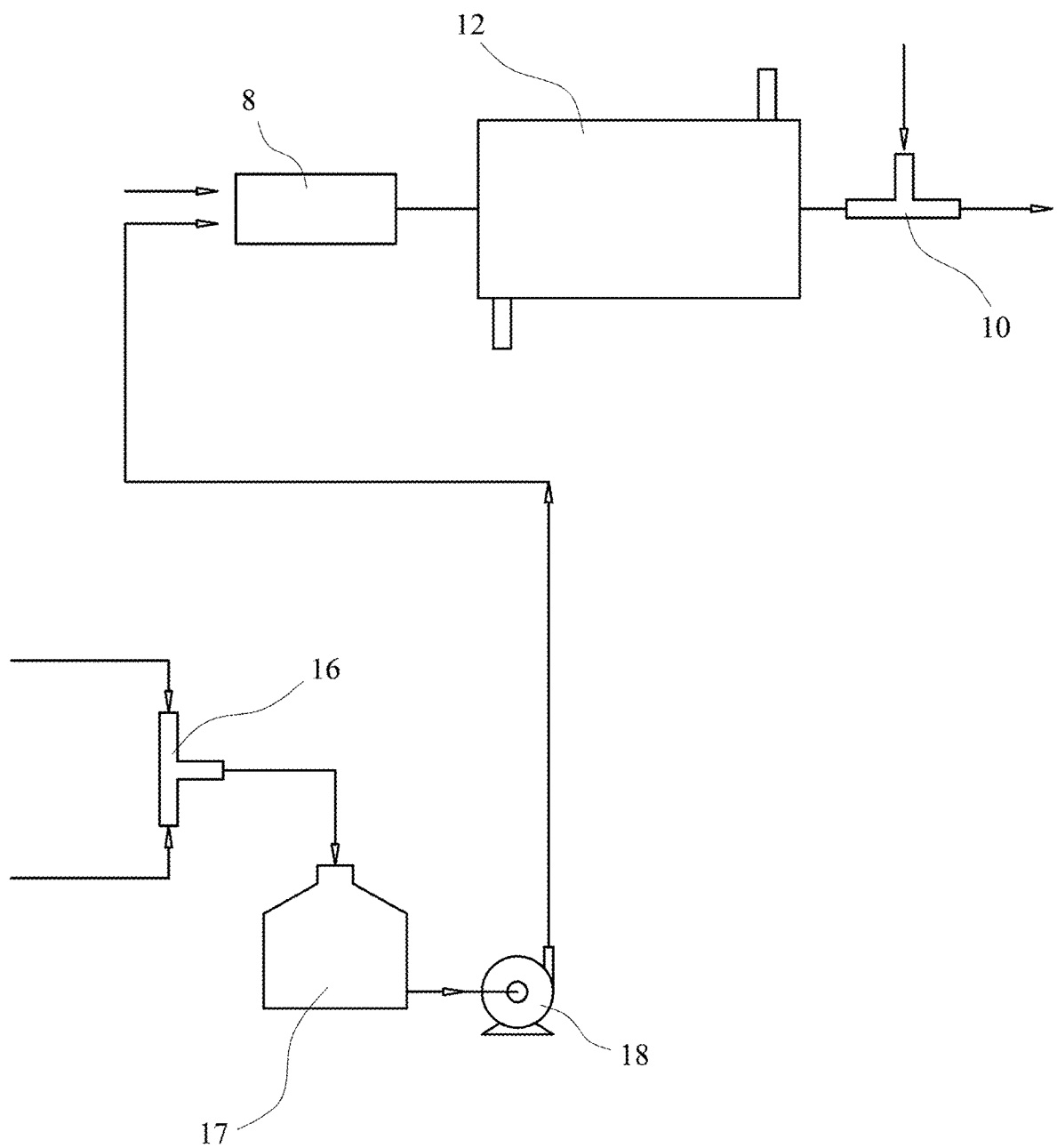
FIG. 6 is a schematic diagram of a micro-reaction system in accordance with an embodiment of the disclosure.

Provided herein was a method for preparing L-carnitine using a micro-reaction system as shown in FIG. 6, where the micro-reaction system included a third micro-mixer 16, a storage tank 17, a first micro-mixer 8, a plate micro-channel reactor 12, and a second micro-mixer 10 communicated in sequence. The first micro-mixer 8 was shown in FIG. 1. The plate micro-channel reactor 12 was made of a 316L stainless steel. The plate micro-channel reactor 12 was a Chemtrix Protrix® micro reactor with a reaction fluid channel, which had a cross section of 250 μm (width)×350 μm (length), a hydraulic diameter of 292 μm, and a total volume of 9.6 mL. The second micro-mixer 10 and the third micro-mixer were both a T-type mixer.

The method was specifically described as follows.

(1) An aqueous sodium hydroxide solution with a mass percentage concentration of 7.11% and an aqueous hydrochloric acid solution with a mass percentage concentration of 10% were prepared. Trimethylamine gas and the aqueous sodium hydroxide solution were transported to the third micro-mixer 16 and mixed, where flow rates of the trimethylamine gas and the aqueous sodium hydroxide solution were controlled to obtain an aqueous trimethylamine solution with a mass percentage concentration of 16.8% which was stored in a storage tank 17.

(2) The sodium hydroxide-containing trimethylamine solution prepared in step (1) and ethyl (R)-4-chloro-3-hydroxybutyrate were pumped into the first micro-mixer 8 at the same time and mixed, where volume flow rates of the two reactants were adjusted separately to ensure that a molar ratio of ethyl (R)-4-chloro-3-hydroxybutyrate to trimethylamine was 0.31:1.

(3) After flowing out of the first micro-mixer 8, the reaction mixture immediately entered the reaction fluid channel of the plate micro-channel reactor 12 and underwent continuous quaternization and hydrolysis while flowing in the tubular micro-channel reactor 9, where a temperature in the reaction fluid channel was 12° C., and a back pressure was 0.6 MPa. After residing for 7.6 min, the reaction mixture was discharged from the outlet of the tubular micro-channel reactor 9.

(4) The reaction mixture flowing out of the reaction fluid channel entered the second micro-mixer 10. At the same time, the aqueous hydrochloric acid solution with a mass percentage concentration of 10% was pumped into the second micro-mixer 10 and adjusted in the flow rate to adjust pH of the reaction mixture to 6 to obtain L-carnitine.

Contents of the substrate and the target compound in the resultant reaction mixture were analyzed by LC (Agilent) based on peak area. The results showed that the substrate (R)-4-halo-3-hydroxybutyrate experienced a complete conversion, and the target compound L-carnitine had a yield of 96.1%. Moreover, a total pressure drop of the first micro-mixer 8, the tubular micro-channel reactor 9 and the second micro-mixer 10 was 0.09 MPa.

The above Examples 1-6 employed the same first micro-mixer 8, of which the structural parameters were presented as follows. The hydraulic diameter of the micro pores 7 in the first micro-mixer 8 for communicating the first liquid inlet channel 1 with the second liquid inlet channel 2 was 30 μm, and a distance between two adjacent micro pores was also 30 μm. The first liquid inlet channel 1 had a rectangular cross section, which had a length of 600 μm and a width of 300 μm. The first liquid inlet channel 1 had a hydraulic diameter of 400 μm, and a length of 10 mm. The second inlet channel 2 had a rectangular cross section, which had a length of 600 μm and a width of 300 μm. The second liquid inlet channel 2 had a hydraulic diameter of 400 μm, and a length of 30 mm. Opening areas of the micro pores 7 on the wall 6 shared by the first liquid inlet channel 1 and the second liquid inlet channel 2 were 30% of an area of the wall 7.

Example 7

Provided herein was a method for preparing L-carnitine using a micro-reaction system, which was basically the same as the preparation method in Example 1, except that the first micro-mixer used herein was a T-type mixer. The two liquid inlet channels of the first micro-mixer used herein were respectively the same as the first liquid inlet channel 1 and the second liquid inlet channel 2 of the first micro-mixer 8 in Example 1 in terms of the hydraulic diameter. The two liquid inlet channels of the first micro-mixer were perpendicular to each other. (R)-4-halo-3-hydroxybutyrate was used as a dispersed phase, and the aqueous trimethylamine solution containing sodium hydroxide was used as a continuous phase.

Contents of the substrate and the target compound in the resultant reaction mixture were analyzed by LC (Agilent) based on peak area. The results showed that the conversion rate of (R)-4-halo-3-hydroxybutyrate was 76% and the target compound L-carnitine had a yield of 64%.

In the above-mentioned Examples 1-7, it was also feasible that the reaction mixture flowing from the outlet of the micro-channel reactor 9 was directly collected, adjusted to pH 6 with hydrochloric acid, and then quantitatively analyzed by liquid chromatography.

Example 8

Provided herein was a method for preparing L-carnitine using a micro-reaction system, which was the same as that in Example 1, except for the structure of the first micro-mixer. The first micro-mixer 8 provided herein was shown in FIG. 1. The hydraulic diameter of the micro pores 7 provided in the first micro-mixer 8 for communicating the first liquid inlet channel 1 with the second liquid inlet channel 2 was 15 μm, and a distance between two adjacent micro pores was 30 μm. The first liquid inlet channel 1 had a rectangular cross section, of which the length was 600 μm and the width was 300 μm. The first liquid inlet channel 1 had a hydraulic diameter of 400 μm and a length of 10 mm. The second inlet channel 2 had a rectangular cross section, of which the length was 600 μm and the width was 300 μm. The liquid inlet channel 2 had a hydraulic diameter of 400 μm, and a length of 30 mm. Opening areas of the micro pores 7 were 30% of an area of the wall 6 shared by the first liquid inlet channel 1 and the second liquid inlet channel 2.

The method was specifically described as follows.

(1) An aqueous sodium hydroxide solution with a mass percentage concentration of 4.77% and an aqueous hydrochloric acid solution with a mass percentage concentration of 10% were prepared. Trimethylamine gas was introduced into the aqueous sodium hydroxide aqueous solution to prepare an aqueous trimethylamine solution with a mass percentage concentration of 12%.

(2) The sodium hydroxide-containing trimethylamine solution prepared in step (1) and ethyl (R)-4-chloro-3-hydroxybutyrate were pumped into the first micro-mixer 8 at the same time and mixed, where volume flow rates of the two reactants were adjusted separately to ensure that a molar ratio of (R)-4-chloro-3-hydroxybutyrate to trimethylamine was 0.25:1.

(3) After flowing out of the first micro-mixer 8, the reaction mixture immediately entered the tubular micro-channel reactor 9 and underwent continuous quaternization and hydrolysis while flowing in the tubular micro-channel reactor 9, where a temperature in the tubular micro-channel reactor 9 was 10° C., and a back pressure was 0.3 MPa. After residing for 7 min, the reaction mixture was discharged from the outlet of the tubular micro-channel reactor 9.

(4) The reaction mixture flowing out of the tubular micro-channel reactor 9 entered the second micro-mixer 10. At the same time, the aqueous hydrochloric acid solution with a mass percentage concentration of 10% was pumped into the second micro-mixer 10 and adjusted in the flow rate to adjust pH of the reaction mixture to obtain L-carnitine.

Contents of the substrate and the target compound in the resultant reaction mixture were analyzed by LC (Agilent) based on peak area. The results showed that the substrate (R)-4-halo-3-hydroxybutyrate experienced a complete conversion, and the target compound L-carnitine had a yield of 97.6%. Moreover, a total pressure drop of the first micro-mixer 8, the tubular micro-channel reactor 9 and the second micro-mixer 10 was 0.066 MPa.

Example 9

Provided herein was a method for preparing L-carnitine using a micro-reaction system, which was the same as that in Example 1, except for the structure of the first micro-mixer. The first micro-mixer 8 was shown in FIG. 1. The hydraulic diameter of the micro pores 7 in the first micro-mixer 8 for communicating the first liquid inlet channel 1 with the second liquid inlet channel 2 was 40 μm, and a distance between adjacent micro pores was 30 μm. The first liquid inlet channel 1 had a rectangular cross section, of which the length was 600 μm and the width was 300 μm. The first liquid inlet channel 1 had a hydraulic diameter of 400 μm and a length of 10 mm. The second inlet channel 2 had a rectangular cross section, of which the length was 600 μm and the width was 300 μm. The hydraulic diameter of the liquid inlet channel 2 was 400 μm, and the length of the second liquid inlet channel 2 was 30 mm. Opening areas of the micro pores were 30% of an area of the wall 6 shared by the first liquid inlet channel 1 and the second liquid inlet channel 2.

The method was specifically described as follows.

(1) An aqueous sodium hydroxide solution with a mass percentage concentration of 4.77% and an aqueous hydrochloric acid solution with a mass percentage concentration of 10% were prepared. Trimethylamine gas was introduced into the aqueous sodium hydroxide solution to prepare an aqueous trimethylamine solution with a mass percentage concentration of 12%.

(2) The sodium hydroxide-containing trimethylamine solution prepared in step (1) and ethyl (R)-4-chloro-3-hydroxybutyrate were pumped into the first micro-mixer 8 at the same time and mixed, where volume flow rates of the two reactants were adjusted separately to ensure that a molar ratio of ethyl (R)-4-chloro-3-hydroxybutyrate to trimethylamine was 0.25:1.

(3) After flowing out of the first micro-mixer 8, the reaction mixture immediately entered the tubular micro-channel reactor 9 and underwent continuous quaternization and hydrolysis while flowing in the tubular micro-channel reactor 9, where a temperature in the tubular micro-channel reactor 9 was 10° C., and a back pressure was 0.3 MPa. After residing for 7 min, the reaction mixture was discharged from the outlet of the tubular micro-channel reactor 9.

(4) The reaction mixture flowing out of the tubular micro-channel reactor 9 entered the second micro-mixer 10. At the same time, the aqueous hydrochloric acid solution with a mass percentage concentration of 10% was pumped into the second micro-mixer 10 and adjusted in the flow rate to adjust pH of the reaction mixture to 6 to obtain L-carnitine.

Contents of the substrate and the target compound in the resultant reaction mixture were analyzed by LC (Agilent) based on peak area. The results showed that the substrate (R)-4-halo-3-hydroxybutyrate experienced a complete conversion, and the target compound L-carnitine had a yield of 95.1%. Moreover, a total pressure drop of the first micro-mixer 8, the tubular micro-channel reactor 9 and the second micro-mixer 10 was 0.058 MPa.

Example 10

Provided herein was a method for preparing L-carnitine using a micro-reaction system, which was the same as that in Example 1, except for the structure of the first micro-mixer. The first micro-mixer 8 was shown in FIG. 1. The hydraulic diameter of the micro pores 7 in the first micro-mixer 8 for communicating the first liquid inlet channel 1 with the second liquid inlet channel 2 was 150 μm, and a distance between adjacent micro pores was 30 μm. The cross section of the first liquid inlet channel 1 was rectangular, of which the length was 600 μm and the width was 300 μm. The hydraulic diameter of the first liquid inlet channel 1 was 400 μm, and the length of the first inlet channel 1 was 10 mm. The second inlet channel 2 had a rectangular cross section, of which the length was 600 μm, and the width was 300 μm. The liquid inlet channel 2 had a hydraulic diameter of 400 μm and a length of 30 mm. Opening areas of the micro pores 7 were 30% of an area of the wall 6 shared by the first liquid inlet channel 1 and the second liquid inlet channel 2.

The method was specifically described as follows.

(1) An aqueous sodium hydroxide solution with a mass percentage concentration of 4.77% and an aqueous hydrochloric acid solution with a mass percentage concentration of 10% were prepared. Trimethylamine gas was introduced into the aqueous sodium hydroxide solution to prepare an aqueous trimethylamine solution with a mass percentage concentration of 12%.

(2) The sodium hydroxide-containing trimethylamine solution prepared in step (1) and ethyl (R)-4-chloro-3-hydroxybutyrate were pumped into the first micro-mixer 8 at the same time and mixed, where volume flow rates of the two reactants were adjusted separately to ensure that a molar ratio of ethyl (R)-4-chloro-3-hydroxybutyrate to trimethylamine was 0.25:1.

(3) After flowing out of the first micro-mixer 8, the reaction mixture immediately entered the tubular micro-channel reactor 9 and underwent continuous quaternization and hydrolysis while flowing in the tubular micro-channel reactor 9, where a temperature in the tubular micro-channel reactor 9 was 10° C., and a back pressure was 0.3 MPa. After residing for 7 min, the reaction mixture was discharged from the outlet of the tubular micro-channel reactor 9.

(4) The reaction mixture flowing out of the tubular micro-channel reactor 9 entered the second micro-mixer 10. At the same time, the aqueous hydrochloric acid solution with a mass percentage concentration of 10% was pumped into the second micro-mixer 10 and adjusted in the flow rate to adjust pH of the reaction mixture to 6 to obtain L-carnitine.

Contents of the substrate and the target compound in the resultant reaction mixture were analyzed by LC (Agilent) based on peak area. The results showed that the (R)-4-halo-3-hydroxybutyrate was 86%, and the target compound L-carnitine had a yield of 73%. Moreover, a total pressure drop of the first micro-mixer 8, the tubular micro-channel reactor 9 and the second micro-mixer 10 was 0.046 MPa.

Example 11

Provided herein was a method for preparing L-carnitine using a micro-reaction system, which was the same as that in Example 1, except for the structure of the first micro-mixer. The first micro-mixer 8 was shown in FIG. 1. The hydraulic diameter of the micro pores 7 in the first micro-mixer 8 for communicating the first liquid inlet channel 1 with the second liquid inlet channel 2 was 30 μm, and a distance between adjacent micro pores was 60 μm. The cross section of the first liquid inlet channel 1 was rectangular, of which the length was 600 μm and the width was 300 μm. The first liquid inlet channel 1 had a hydraulic diameter of 400 μm, and a length of 10 mm. The second inlet channel 2 had a rectangular cross section, of which the length was 600 μm and the width was 300 μm. The liquid inlet channel 2 had a hydraulic diameter of 400 μm, and a length of 30 mm. Opening areas of the micro pores 7 were 30% of an area of the wall 6 shared by the first liquid inlet channel 1 and the second liquid inlet channel 2.

The method was specifically described as follows.

(1) An aqueous sodium hydroxide solution with a mass percentage concentration of 4.77% and an aqueous hydrochloric acid solution with a mass percentage concentration of 10% were prepared. Trimethylamine gas was introduced into the aqueous sodium hydroxide solution to prepare an aqueous trimethylamine solution with a mass percentage concentration of 12%.

(2) The sodium hydroxide-containing trimethylamine solution prepared in step (1) and ethyl (R)-4-chloro-3-hydroxybutyrate were pumped into the first micro-mixer 8 at the same time and mixed, where volume flow rates of the two reactants were adjusted separately to ensure that a molar ratio of ethyl (R)-4-chloro-3-hydroxybutyrate to trimethylamine was 0.25:1.

(3) After flowing out of the first micro-mixer 8, the reaction mixture immediately entered the tubular micro-channel reactor 9 and underwent continuous quaternization and hydrolysis while flowing in the tubular micro-channel reactor 9, where a temperature in the tubular micro-channel reactor 9 was 10° C., and a back pressure was 0.3 MPa. After residing for 7 min, the reaction mixture was discharged from the outlet of the tubular micro-channel reactor 9.

(4) The reaction mixture flowing out of the tubular micro-channel reactor 9 entered the second micro-mixer 10. At the same time, the aqueous hydrochloric acid solution with a mass percentage concentration of 10% was pumped into the second micro-mixer 10 and adjusted in the flow rate to adjust pH of the reaction mixture to 6 to obtain L-carnitine.

Contents of the substrate and the target compound in the resultant reaction mixture were analyzed by LC (Agilent) based on peak area. The results showed that the substrate (R)-4-halo-3-hydroxybutyrate experienced a complete conversion, and the target compound L-carnitine had a yield of 95.8%. Moreover, a total pressure drop of the first micro-mixer 8, the tubular micro-channel reactor 9 and the second micro-mixer 10 was 0.06 MPa.

Example 12

Provided herein was a method for preparing L-carnitine using a micro-reaction system, which was the same as that in Example 1, except for the structure of the first micro-mixer. The first micro-mixer 8 was shown in FIG. 1. The hydraulic diameter of the micro pores 7 in the first micro-mixer 8 for communicating the first liquid inlet channel 1 with the second liquid inlet channel 2 is 30 μm, and a distance between adjacent micro pores was 30 μm. The first liquid inlet channel 1 had a rectangular cross section, of which the length was 600 μm and the width was 300 μm. The first liquid inlet channel 1 had a hydraulic diameter of 400 μm and a length of 10 mm. The second inlet channel 2 had a rectangular cross section, of which the length was 600 μm and the width was 300 μm. The liquid inlet channel 2 had a hydraulic diameter of 400 μm, and a length of 30 mm. Opening areas of the micro pores 7 were 40% of an area of the wall 6 shared by the first liquid inlet channel 1 and the second liquid inlet channel 2.

The method was specifically described as follows.

(1) An aqueous sodium hydroxide solution with a mass percentage concentration of 4.77% and an aqueous hydrochloric acid solution with a mass percentage concentration of 10% were prepared. Trimethylamine gas was introduced into the aqueous sodium hydroxide solution to prepare an aqueous trimethylamine solution with a mass percentage concentration of 12%.

(2) The sodium hydroxide-containing trimethylamine solution prepared in step (1) and ethyl (R)-4-chloro-3-hydroxybutyrate were pumped into the first micro-mixer 8 at the same time and mixed, where volume flow rates of the two reactants were adjusted separately to ensure that a molar ratio of ethyl (R)-4-chloro-3-hydroxybutyrate to trimethylamine was 0.25:1.

(3) After flowing out of the first micro-mixer 8, the reaction mixture immediately entered the tubular micro-channel reactor 9 and underwent continuous quaternization and hydrolysis while flowing in the tubular micro-channel reactor 9, where a temperature in the tubular micro-channel reactor 9 was 10° C., and a back pressure was 0.3 MPa. After residing for 7 min, the reaction mixture was discharged from the outlet of the tubular micro-channel reactor 9.

(4) The reaction mixture flowing out of the tubular micro-channel reactor 9 entered the second micro-mixer 10. At the same time, the aqueous hydrochloric acid solution with a mass percentage concentration of 10% was pumped into the second micro-mixer 10 and adjusted in the flow rate to adjust pH of the reaction mixture to 6 to obtain L-carnitine.

Contents of the substrate and the target compound in the resultant reaction mixture were analyzed by LC (Agilent) based on peak area. The results showed that the substrate (R)-4-halo-3-hydroxybutyrate experienced a complete conversion, and the target compound L-carnitine had a yield of 96.2%. Moreover, a total pressure drop of the first micro-mixer 8, the tubular micro-channel reactor 9 and the second micro-mixer 10 was 0.058 MPa.

Comparative Example 1

In this comparative example, the preparation of L-carnitine was performed in a batch reactor, and specifically, the batch reactor was a 100 mL round-bottomed flask. The preparation was specifically described as follows. The round-bottomed flask was placed in a 10° C. water bath, and then sequentially added with 34 mL of an aqueous trimethylamine solution (containing 4.2% by weight of sodium hydroxide) with a mass percentage concentration of 12%, and 2.42 mL of ethyl (R)-4-chloro-3-hydroxybutyrate for reaction. The reaction mixture was regularly sampled for analysis, and the results demonstrated that the reaction substrate ethyl (R)-4-chloro-3-hydroxybutyrate achieved a conversion of about 56% after 1 hour; about 73% after 2 hours; about 86% after 3 hours; and about 97% after 7 hours, and after 7 hours, the product L-carnitine achieved a yield of 77%.

Comparative Example 2

In this comparative example, the preparation of L-carnitine was performed in a batch reactor, and specifically, the batch reactor was a 250 mL round-bottomed flask. The preparation was specifically described as follows. The round-bottomed flask was placed in a 15° C. water bath, and then sequentially added with 70 mL of an aqueous trimethylamine solution (containing 4.05% by weight of sodium hydroxide) with a mass percentage concentration of 10%, and 5.76 mL of butyl (R)-(+)-4-chloro-3-hydroxybutyrate for reaction. The reaction mixture was regularly sampled for analysis, and the results demonstrated that the reaction substrate (R)-(+)-4-chloro-3-hydroxybutyrate achieved a conversion of about 35% after 1 hour; about 52% after 2 hours; about 61% after 3 hours; about 76% after 8 hours; and about 98% after 17 hours, and after 17 hours, the product L-carnitine achieved a yield of 77%.

The Comparative Example 1 and Example 1 had the same ratio of the (R)-4-chloro-3-hydroxybutyrate to trimethylamine, and the Comparative Example 2 and Example 4 were the same in the ratio of the (R)-4-chloro-3-hydroxybutyrate to trimethylamine. Compared to the batch stirred reactor, the micro-reaction system provided herein can greatly shorten the reaction time, greatly suppress the side reactions, and significantly improve the yield of L-carnitine.

It should be noted that described above are merely preferred embodiments of the invention, which are not intended to limit the invention. It should be understood that any modification, change and replacement made by those skilled in the art without departing from the spirit of the invention should fall within the scope of the invention defined by the appended claim.

What is claimed is:

1. A method for preparing L-carnitine using a micro-reaction system, the micro-reaction system comprising a first micro-mixer and a micro-channel reactor in communication; the method comprising:
    (1) pumping a (R)-4-halo-3-hydroxybutyrate and an aqueous trimethylamine solution containing an inorganic base into the first micro-mixer simultaneously followed by mixing to obtain a mixture; and
    (2) allowing the mixture flowing out of the first micro-mixer to enter the micro-channel reactor; and subjecting the mixture to continuous quaternization and hydrolysis to obtain the L-carnitine;
    wherein the (R)-4-halo-3-hydroxybutyrate is shown in formula (I)

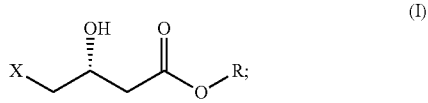

(I)

wherein X is F, Cl, Br or I, and R is a $C_1$-$C_4$ alkyl.

2. The method of claim 1, wherein in step (1), the (R)-4-halo-3-hydroxybutyrate is ethyl (R)-4-chloro-3-hydroxybutyrate; and the inorganic base is an alkali metal carbonate, an alkali metal hydroxide or a combination thereof.

3. The method of claim 1, wherein in step (1), a molar ratio of (R)-4-halo-3-hydroxybutyrate to trimethylamine is (0.1-5):1; and a molar ratio of (R)-4-halo-3-hydroxybutyrate to the inorganic base is (0.2-1.2):1.

4. The method of claim 1, wherein in step (1), the aqueous trimethylamine solution comprises 3%-45% by weight of trimethylamine.

5. The method of claim 1, wherein in step (2), a temperature in the micro-channel reactor is −40° C.-100° C., and a residence time of the reaction mixture in the micro-channel reactor is 0.2-30 min.

6. The method of claim 1, wherein in step (2), a back-pressure in the micro-channel reactor is 0.1-3 MPa.

7. The method of claim 1, further comprising:
    adjusting the mixture flowing out of the micro-channel reactor to pH 6-8 with a pH regulator.

8. The method of claim 7, wherein the micro-reaction system further comprises a second micro-mixer; an outlet of the micro-channel reactor is communicated with an inlet of the second micro-mixer; and the pH adjustment is carried out in the second micro-mixer.

9. The method of claim 8, wherein a total pressure drop of the first micro-mixer, the micro-channel reactor and the second micro-mixer is 0-0.7 MPa.

10. The method of claim 1, wherein the first micro-mixer comprises a first liquid inlet channel and a second liquid inlet channel parallel to each other; one end of the first liquid inlet channel is provided with a first liquid inlet, and the other end of the first liquid inlet channel is closed; one end of the second liquid inlet channel is provided with a second liquid inlet, and the other end of the second liquid inlet channel is provided with a liquid outlet; the first liquid inlet and the second liquid inlet are arranged at the same end; a wall is shared by the first liquid inlet channel and the second liquid inlet channel, and a plurality of micro pores are provided at the wall to communicate the first liquid inlet channel with the second liquid inlet channel;
    in step (1), the (R)-4-halo-3-hydroxybutyrate is pumped into the first liquid inlet channel, and the aqueous trimethylamine solution containing the inorganic base is pumped into the second liquid inlet channel; the (R)-4-halo-3-hydroxybutyrate in the first liquid inlet channel flows through the micro pores into the second liquid inlet channel, and then is mixed with the aqueous trimethylamine solution containing the inorganic base in the second liquid inlet channel.

11. The method of claim 10, wherein the micro pores are circular.

12. The method of claim 10, wherein a hydraulic diameter of each of the plurality of micro pores is 0.1-300 μm, and a distance between adjacent two micro pores is 0.1 μm-1.5 mm.

13. The method of claim 10, wherein opening areas of the plurality of micro pores are 1%-70% of an area of the wall.

14. The method of claim 10, wherein a cross section of the first liquid inlet channel is circular or rectangular, and a cross section of the second liquid inlet channel is circular or rectangular.

15. The method of claim 10, wherein a hydraulic diameter of the first liquid inlet channel is 0.01-20 mm, and a hydraulic diameter of the second liquid inlet channel is 0.01-20 mm.

16. The method of claim 10, wherein a ratio of the hydraulic diameter of each of the plurality of micro pores to the hydraulic diameter of the second liquid inlet channel is 0.0001-0.1:1.

17. The method of claim 10, wherein a length of the first liquid inlet channel is 2-30 mm, and a length of the second liquid inlet channel is 4-100 mm.

18. The method of claim 1, wherein the micro-channel reactor is a tubular micro-channel reactor or a plate micro-channel reactor.

19. The method of claim 18, wherein an inner diameter of the tubular micro-channel reactor is 100 μm-10 mm.

20. The method of claim 18, wherein a hydraulic diameter of a reaction fluid channel of the plate micro-channel reactor is 100 μm-10 mm.

* * * * *